United States Patent [19]
Stroupe

[11] Patent Number: 5,321,984
[45] Date of Patent: Jun. 21, 1994

[54] AUTOMATIC SAMPLE CONTROL CART

[75] Inventor: Michael L. Stroupe, Durham, N.C.

[73] Assignee: Graseby Holdings Corporation, Durham, N.C.

[21] Appl. No.: 974,790

[22] Filed: Nov. 12, 1992

[51] Int. Cl.$^5$ .............................................. G01N 1/00
[52] U.S. Cl. .................................................. 73/863.11
[58] Field of Search ........... 73/863.01, 863.11, 863.12, 73/863.21, 863.23, 863.31, 863.33, 864, 864.31, 864.34, 864.51, 864.52, 863.81, 863.83, 864.35, 863.52, 864.33, 864.62, 863.83, 863.86, 864.91

[56] References Cited

U.S. PATENT DOCUMENTS

| | | | |
|---|---|---|---|
| 3,793,887 | 2/1974 | Anderson et al. | 73/863.11 |
| 3,846,075 | 11/1974 | Cioffi | 73/863.33 |
| 4,274,285 | 6/1981 | Purgold | 73/863.31 |
| 4,336,721 | 6/1982 | Curtis | 73/863.11 |
| 4,377,949 | 3/1983 | Tucker et al. | 73/863.31 |
| 4,454,773 | 6/1984 | Brunner et al. | 73/863.31 |
| 4,704,910 | 11/1987 | Conrad | 73/863.31 |
| 4,813,984 | 3/1989 | Griffis | 73/864.34 |
| 5,011,517 | 4/1991 | Cage et al. | 73/863.11 |

FOREIGN PATENT DOCUMENTS

| | | | |
|---|---|---|---|
| 3257364 | 11/1991 | Japan | 73/864.51 |
| 215591 | 4/1968 | U.S.S.R. | 73/863.33 |

OTHER PUBLICATIONS

Lourence et al., "Flexible Bags Collect Gas Samples", Control Engineering, vol. 14 #9, Sep. 1967, p. 105.

*Primary Examiner*—Robert Raevis
*Attorney, Agent, or Firm*—Olive & Olive

[57] ABSTRACT

An autosampling device for use in sampling air with canisters and analyzing the contents of said canisters for the presence of pollutants which allows random access of the contents of the canisters and controlled direction of the canister contents to a cryogenic concentrator. The device is a cart having shelf members for holding a plurality of canisters. Sample lines are mounted on the cart to be connectable to a canister at one end of said lines and to an inlet port of an electrically actuated multiposition valve at the other end. To protect against sample disruption, a heated zone around the valve controls valve temperature. An outlet sample line enclosed in a heated zone extends from an outlet port on the valve and is connectable to an inlet of the cryogenic concentrator. Selection of specific samples by means of a multiposition valve and the temperatures of the two heated zones may be controlled by connection to a programmed computer, and thermocouple feedback from the cart to the computer may also be provided.

8 Claims, 6 Drawing Sheets

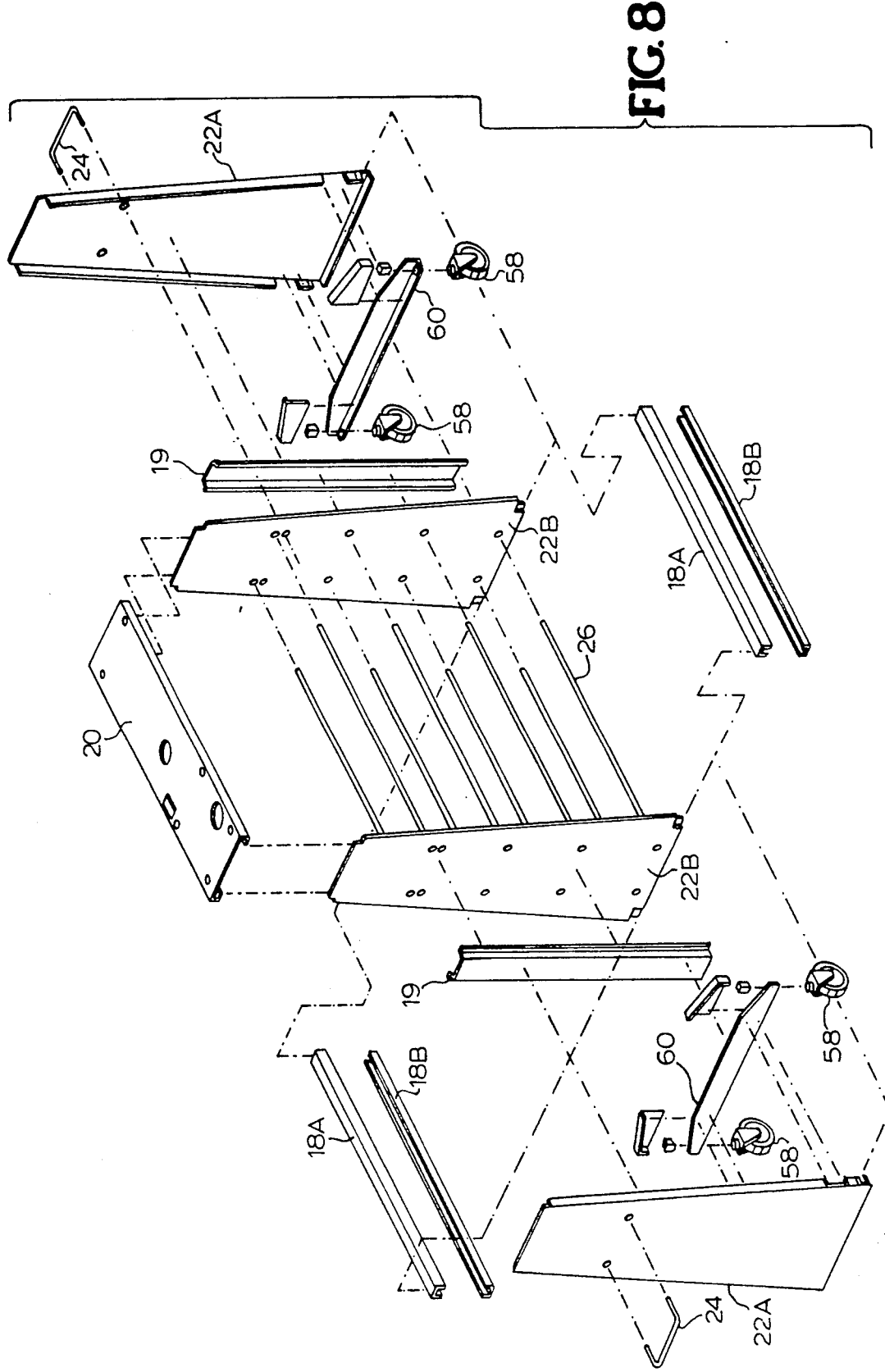

AUTOMATIC SAMPLE CONTROL CART

BACKGROUND OF THE INVENTION

1. Field of the Invention

This invention relates to analytical apparatuses and methods for volatile organic compounds, and in particular, relates to air sampling and analysis utilizing a cryogenic concentrator and a gas chromatograph/mass spectrometer or gas chromatograph with multiple detectors.

2. Description of the Related Art

Environmental concerns about air pollution have led to the need for reliable, sensitive analytical methods for the identification of toxic or other undesirable volatile organic compounds (VOCs). Individuals, companies, and governmental entities at all levels often have a need to detect, identify and quantitate unknown or suspected air pollutants.

The use of canisters, TEDLAR TM bags and other standardized containers to sample air has proven to be an effective and efficient collection method in the analysis of air pollutants. The standard method is summarized in the EPA *Compendium of Methods for the Determination of Toxic Organic Compounds in Ambient Air* (Method TO-14).

In Method TO-14, ambient air samples are collected in pre-evacuated SUMMA passivated canisters. After collection, the sample canister pressure may be above or below atmospheric pressure. Sample canisters are tagged with identification including pressure reading and transported to a specified site for analyses.

Before being analyzed, individual canisters at subatmospheric pressure may be pressurized to 20 psig with zero dry nitrogen. The resulting dilution is calculated based on the fixed volume of the can (i.e. six liters) and the pressure readings of the canister before and after the dilution with nitrogen.

Sample canisters are connected to the inlet of the analytical system. A pressurized sample canister may require a split of an established flow from the canister to deliver a specified mass flow controlled rate (i.e. 40 ml/min) to the concentrating section of the analytical system. Water vapor is reduced in the gas stream by a NAFION TM dryer. The VOCs are selectively concentrated by condensation in a reduced temperature (cryogenic) trap, while the main components of air (nitrogen and oxygen) are not retained.

Once the pre-determined volume of sample is concentrated on the cryogenic trap, the trap is rapidly heated. The VOCs are revolatilized and introduced to a GC column through a heated transfer line. The gas chromatographic capillary column recommended in Method TO-14 is cooled to a sub-ambient temperature (i.e. −50° C.) to focus (minimize the volume of) the VOCs. An appropriate GC temperature program heats the GC oven containing the capillary column used to separate the sample components. Each component is detected by one or more detectors for identification and quantitation.

The canisters used for sampling atmospheric gases are generally made of stainless steel and have a volume of six liters at atmospheric pressure. Each sample and control requires a separate canister. After the sample collecting is accomplished, the canisters are typically piled in boxes or individually carried back to the site of the cryogenic concentrator and GC/MS in the laboratory. The canisters are individually connected in sequence to an inlet port on a multiposition valve to begin the processing. As is readily understood, the transport and repeated individual connecting are cumbersome and time-consuming operations.

It is therefore an object of this invention to provide a mobile device on which a plurality of canisters may be placed and transported.

It is a further object of this invention to provide a device having sample lines for a plurality of canisters to be connected to a multiposition controllable selective outlet.

It is a further object of this invention to provide a device and method enabling sample chain-of-custody determination. Other objects and advantages will be more fully apparent from the following disclosure and appended claims.

SUMMARY OF THE INVENTION

The cart of the invention is an autosampling device for use in sampling air, utilizing canisters which are preferably spherical in shape, and in analyzing the contents of said canisters for the presence of pollutants. As used herein, the word "canister" includes any standard gas collection container such as standard stainless steel canisters, TEDLAR TM bags and the like which may be placed on the cart of the invention.

The cart allows random, controlled access of the contents of the canisters and controlled connection of the canister contents to a concentrator, for example, a cryogenic concentrator. The cart has shelf members for securely holding a plurality of canisters. Sample lines mounted on the cart are connectable to each canister at one end and to each inlet port of an electronically actuated multiposition valve at the other end. To protect the samples from changes in temperature which may alter gas flow rate, the sample outlet line is heated. A sample outlet line which is enclosed in another heated zone extends from an outlet port on the multiposition valve and is connectable to an inlet port of the cryogenic concentrator. The position of the multiposition valve and the temperatures of the two heated zones may be controlled by connection to the cryogenic concentrator. Thermocouple feedback from the cart to the cryogenic concentrator may also be provided through the connection.

Other aspects and features of the invention will be more fully apparent from the following disclosure and appended claims.

BRIEF DESCRIPTION OF THE DRAWINGS

FIG. 8 is an exploded view of the parts used to assemble the embodiment of the cart shown in FIG. 1.

DETAILED DESCRIPTION OF THE INVENTION AND PREFERRED EMBODIMENTS THEREOF

Figure 1:
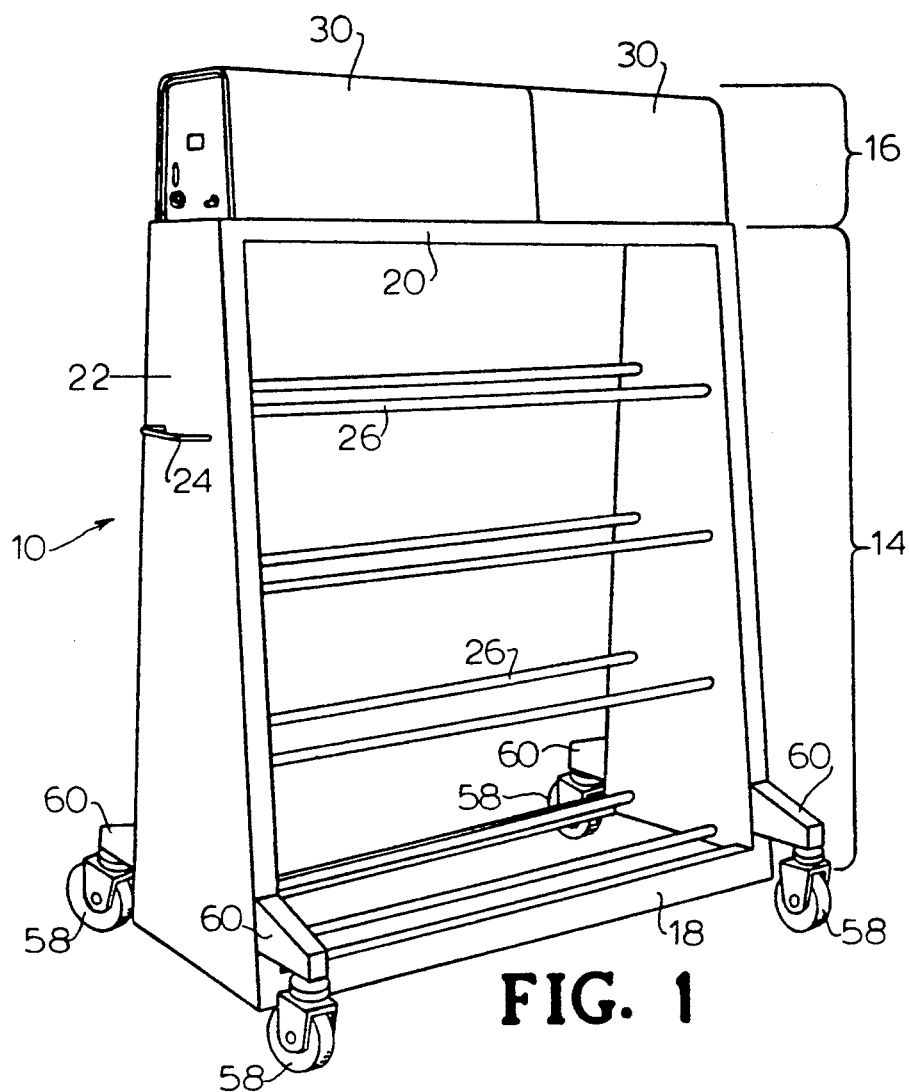
FIG. 1 is a perspective view of a preferred embodiment of the cart of the invention without canisters.
Figure 3:
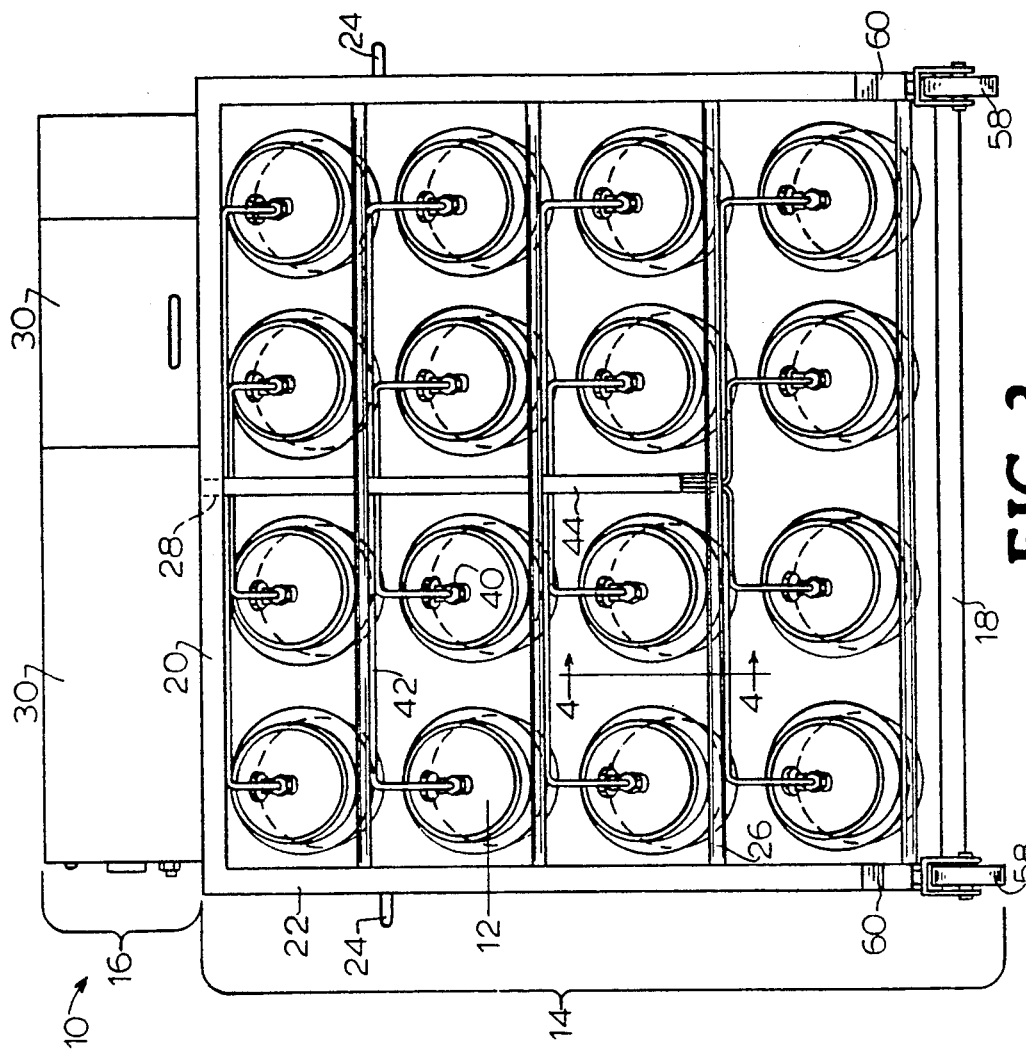
FIG. 3 is a side elevation view of the cart of FIG. 1 with canisters in place and connecting lines.
Figure 2:
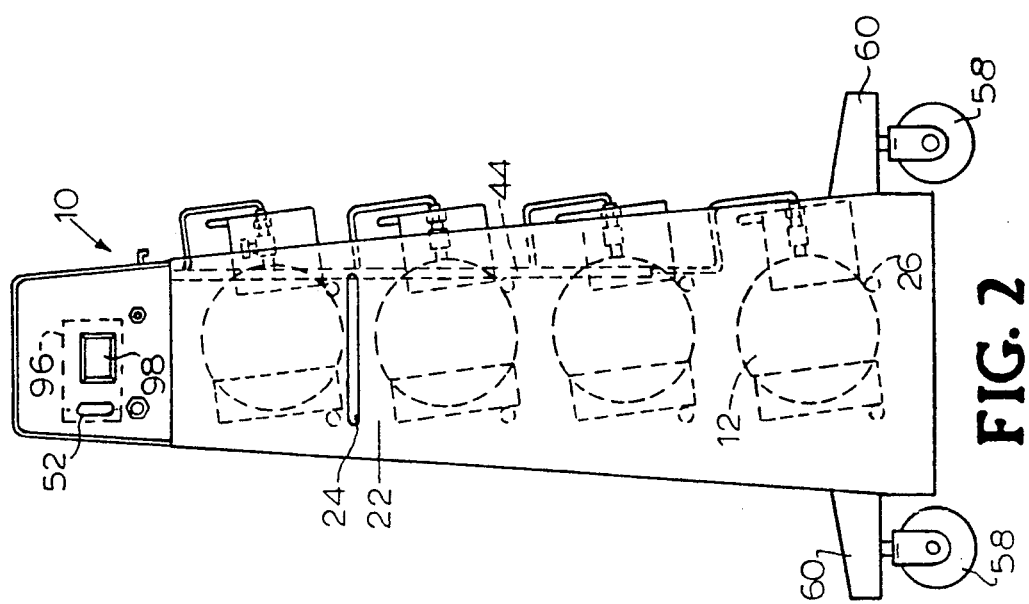
FIG. 2 is an end elevation view of the cart of FIG. 1 with canisters in place.

The present invention is a VOC AUTOSAMPLER TM, an automatic sample mobile control cart for transporting and/or holding a plurality of canisters which are used for identification of toxic or other undesirable volatile organic compounds. The cart 10 as illustrated in FIGS. 1, 2, 3 may be used to collect samples at a sampling site and then moved to the site of a cryogenic concentrator so that samples may be selectively removed from the canisters 12 as needed. The contents of the canisters 12 may be randomly and selectively accessed through an electronically actuated and heated VALCO Multiposition 16-to-1 valve (Valco Instruments, Inc. Houston, Tex.) and then the sample directed through a heated line to the sample outlet port of the multiposition valve.

The VOC AUTOSAMPLER TM cart has two main sections, the first of which is called the body 14 of the cart and holds the canisters 12, and the second of which is called the sampling section 16 and contains control components for accessing and handling the samples.

The body 14 of the cart 10 preferably comprises one or more lower transverse structural members 18 extending across the width of the cart 10 between two trapezoidal end panels 22, which are preferably angled backward at their forward edges as shown in FIGS. 1 and 2. As shown in FIG. 8 structural member 18 are preferably made of a plurality of channel stiffeners 18A,B. In addition, a side panel stiffener 19 is preferably added to each side. The body 14 of the cart 10 also preferably comprises a planar rectangularly formed top section parallel to the ground or other surface upon which the cart is placed. A plurality of pairs of canister supporting shelf members 26 are mounted on end panels 22 by means known in the art, and extend parallel to each other between said end panels 22. The pairs of shelf members 26 are spaced vertically a sufficient distance apart so that canisters 12 to be stored on any of the pairs of shelf members 26 can pass between the shelf members 26 o which they are to rest and either the shelf members 26 above the shelf section on which they are to rest or top section 20.

For use with typical six liter canisters 12, the canister supporting shelf members 26 are placed approximately 20 cm (8 in) apart horizontally and 27 cm (10-¾ in) vertically. Four shelf canister-holding locations are provided on each shelf for a total capacity of 16 canisters 12 on the preferred embodiment of the cart 10.

The various components of the cart 10 may be made of any material known in the art which is sufficiently sturdy to hold the canisters 12 and the components in the second portion of the cart 10, for example, metal, wood, plastics, manufactured composite materials, and combinations thereof.

Figure 4:
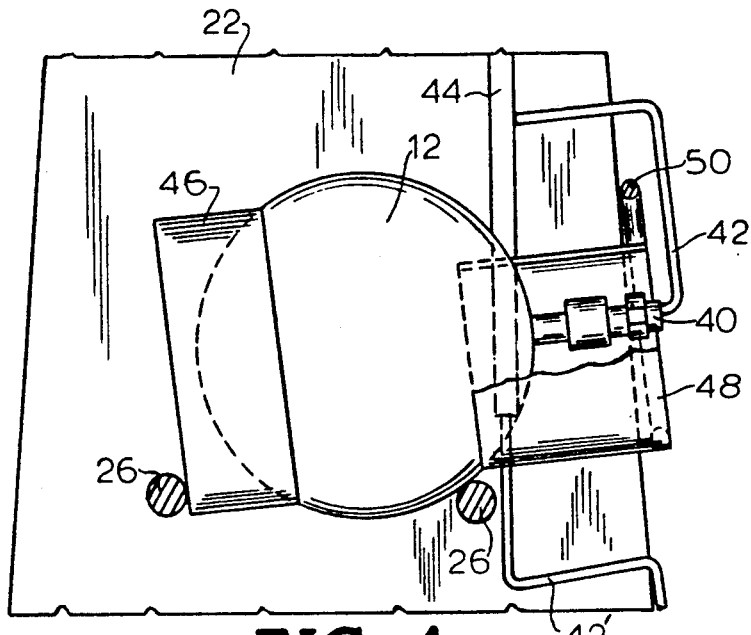
FIG. 4 is a section view taken along line 3—3 of FIG. 2 and having connective tubing attached.

An enlarged detail view of canister 12 is illustrated in FIG. 4. Canister 12 is typically spherical in shape and is supplied with stand 46 s that it may be safely placed on a flat surface. The opposite, or upper end of canister 12 has an attached top cylinder 48 configured around a valved connector 40. Top cylinder 48 has a portion partially cut out so as to form handle 50 for easy lifting. Valved connector 40 is threaded to accept complementary threads on the proximal end of sample line 42 attached thereto.

Tubular gas conducting sample lines 42 extend from each canister-holding location, where they are attached to the valved connector 40 on each canister after the samples have been obtained. The sample lines 42 from the canisters 12 on each set of shelf members 26 extend laterally to one position, preferably an end of the cart 10, and then are held together with sample lines 42 from canisters on other shelf members 26 in one or more line collecting channels 44 and extend upward to the sample handling section 16 at the top of the cart 10. The line collecting channel(s) 44 function to hide and to protect sample lines 42 in the path to sampling section 16 of cart 10.

The grouped sample lines 42 enter the sample handling section through a hole in the top of the cart body 10. Preferably, the sample lines 42 are attached essentially permanently to the shelf members 26 and to the sample handling section 16 so that each canister 12 with a sample may simply be placed at a canister location and attached to the corresponding sample line 42.

Figure 5:
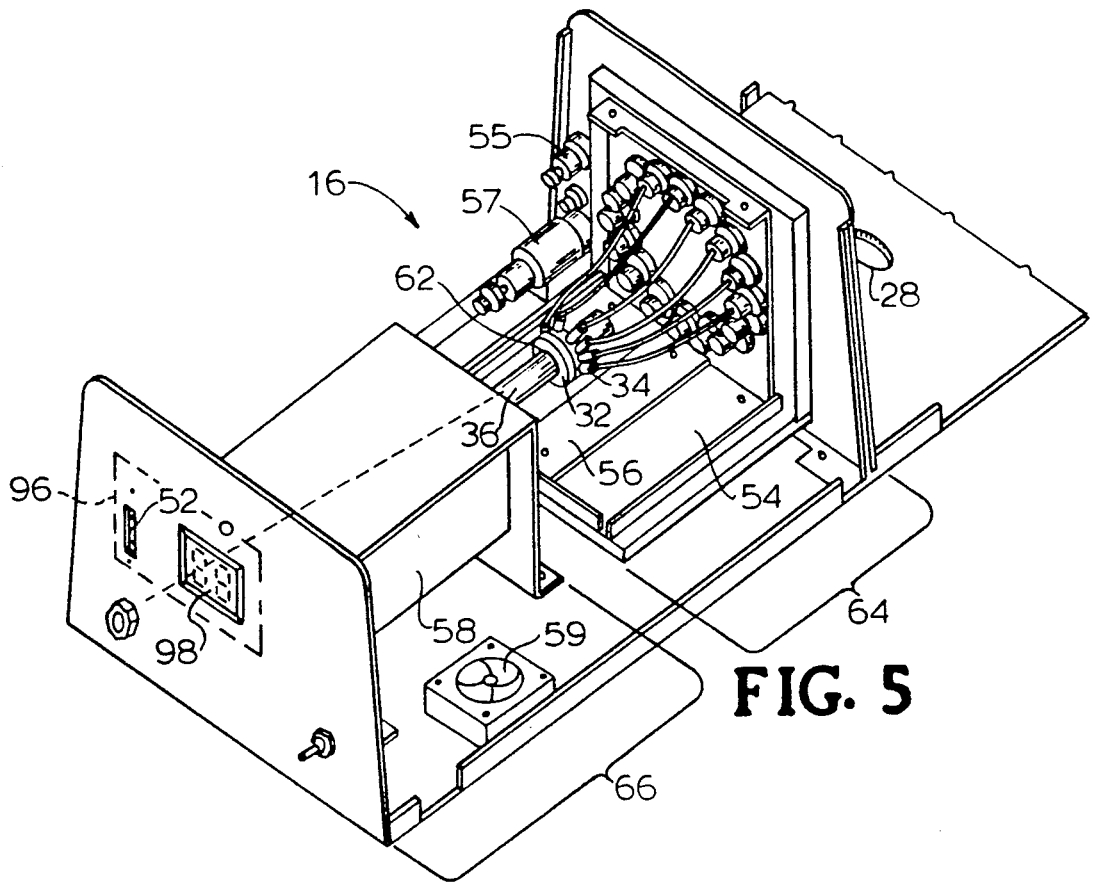
FIG. 5 is a perspective view of the sampling section of the cart of the invention with the connecting lines removed for clarity.

The components of the second portion of the cart, included in sampling section 16, are preferably placed on top of the body portion, and as shown in FIGS. 1, 2 and 3 are preferably covered by a removable cover 30. In the view shown in FIG. 1, the multiposition valve 32, the ends of the grouped sample lines 42, and thermocouple wiring are housed at the left end of the cart 10 under the left portion of the cover 30, so that when the right cover piece is lifted backward on its hinges (not shown), there is an open space for placement of tools next to these components. FIG. 5 is a more detailed perspective view of the sampling section 16 of the cart with its cover 30 and most of the connective tubing removed for clarity.

Figure 6:
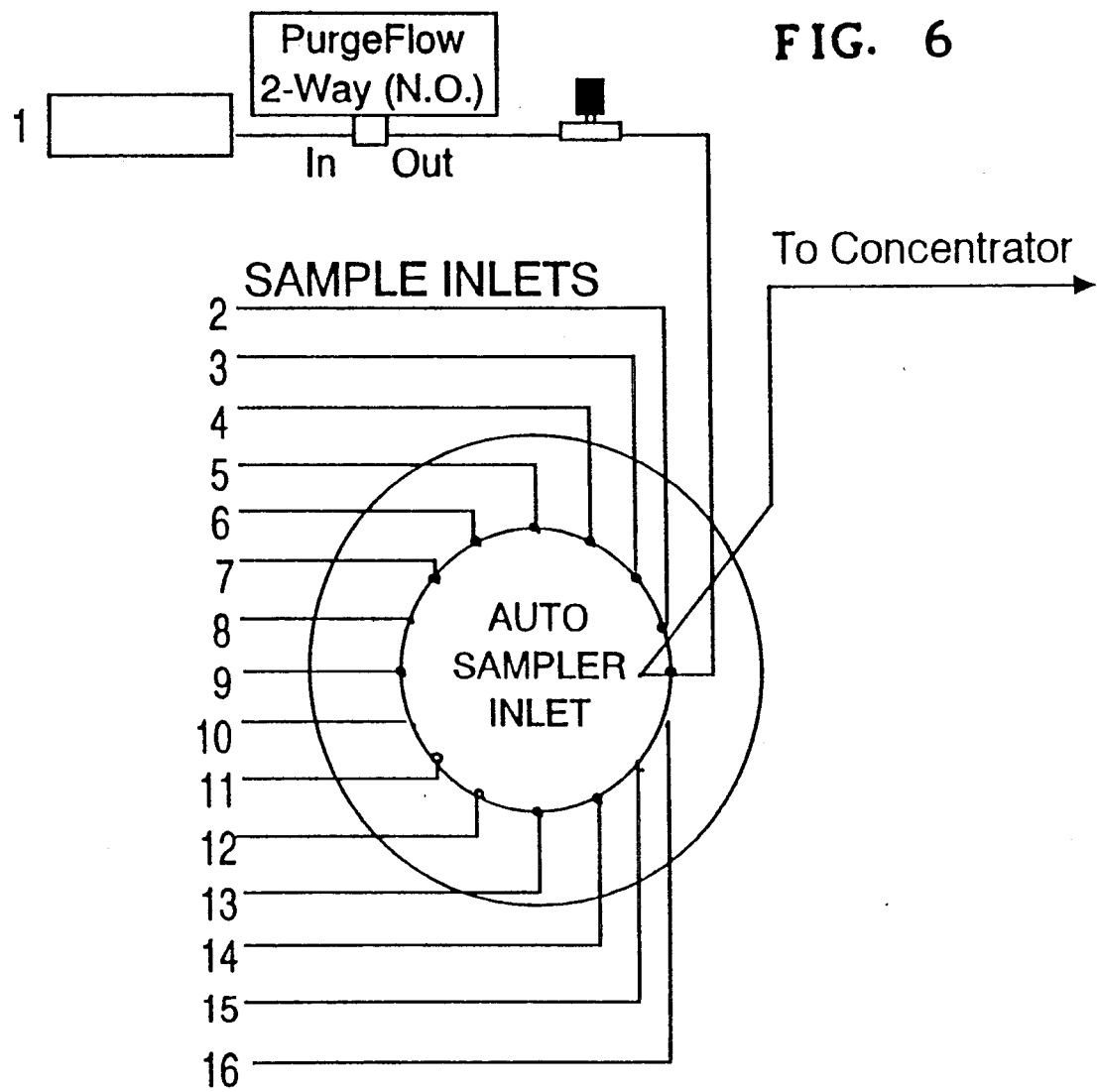
FIG. 6 is a schematic view of the sampling section of the cart of the invention.

The central operative device of sampling section 16 as seen in FIG. 5 is multiposition valve 32. Valve 32 is a selective, servo-controlled multiple port unit having multiple, for example sixteen, inlets 34, in the embodiment shown in FIG. 5, and a single outlet 36. Electrical signals supplied to multiposition valve 32 activate an integral electric actuator operative to position an internal valve spool to selectively connect a particular inlet port 34 to the outlet port 62 and outlet line 36, thereby flowing the sample air from a selected sample canister 12 (FIG. 3) to a downstream chemical analyzer. The outlet line 36 is connected to the analyzer (not shown) by means of additional tubing. A multiposition valve 32 containing 16 inlet parts 34 and one outlet port 62 and outlet line 36 which may be used in the invention herein is available from Valco Instruments Co., Inc. (Houston, Tex.). A schematic diagram of use of the multiposition valve 32 in the invention herein is shown in FIG. 6.

Figure 7:
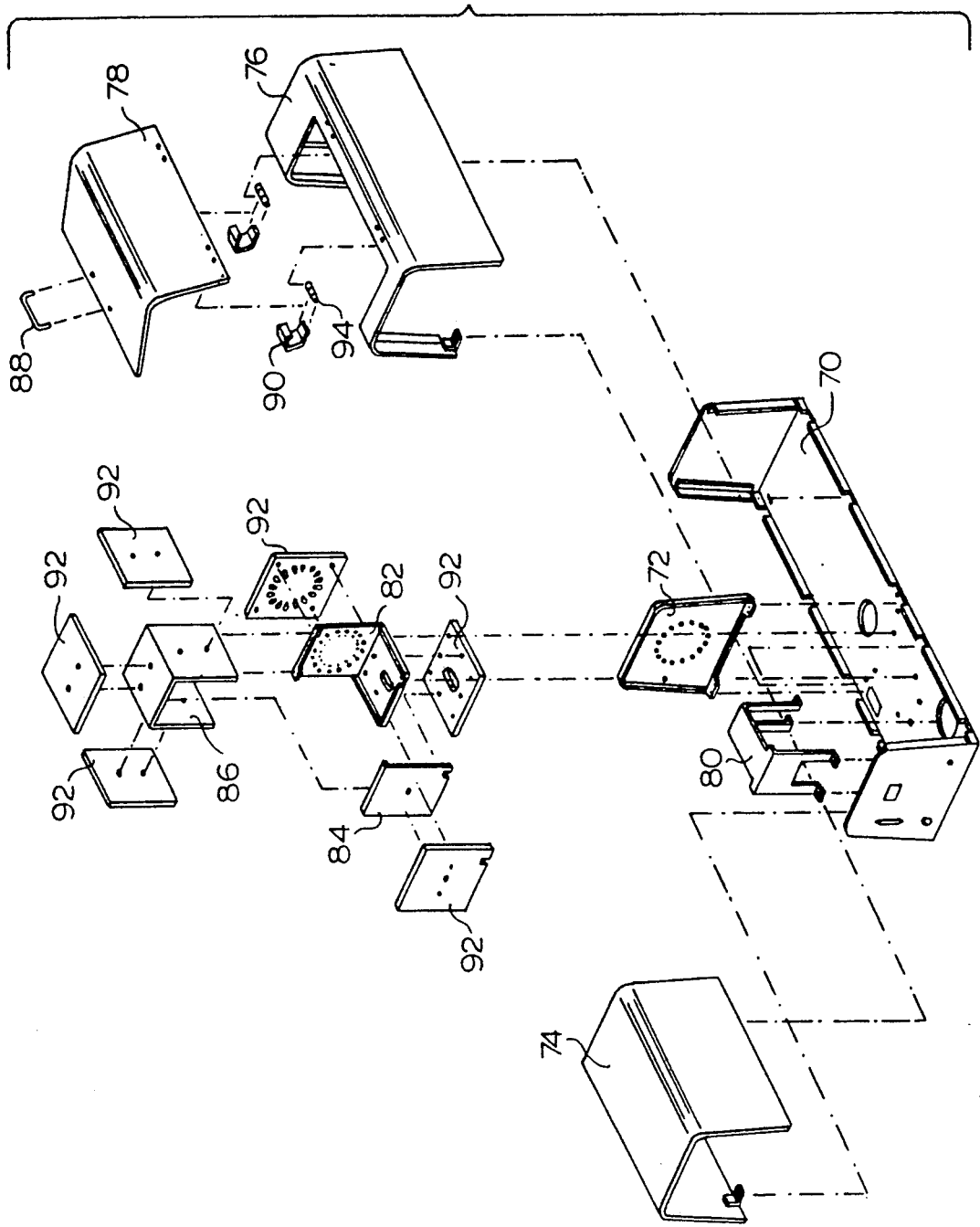
FIG. 7 is an exploded view of the parts used to assemble the sampling section of the cart of the invention.

An exploded view of the parts which may be used to assemble the sample accessing portion and the adjacent covered area is shown in FIG. 7. The assembly includes a base plate 70, a top inlet panel 72, a top front cover 74, a cover 76 for the inlet access and storage area, a door 78 for cover 76, an actuator bracket, an autosampler base 82, an autosample oven back 84 and top 86, handle 88, hinge brackets 90, oven insulation pieces 92, and friction hinges 94.

Preferably the control of selection of inlet ports 34, monitoring to be sure the correct ports are selected and the display of valve position or output of any error signal to the operator is controlled by a preprogrammed circuit board 96, such as is used in the art of switching boards. Display of selected information may be in window 98 or by other means known in the art.

Electrical signals operative to activate valve 32 are transmitted to valve 32 by means of multiple pin connector 52 mounted to a fixed member of sampling section 16, such as an end wall thereof. Appropriate connective wiring is connected from pin connector 52 to valve 32.

In the case of airborne pollutants there may be precipitation or condensation if a significant temperature drop occurs. To reduce this potential, a first heater 54 is employed to control the temperature at and around valve 32. A feedback thermostat 56 for example a Type K thermocouple, is located adjacent valve 32 to read resultant temperature and maintain the desired setting by communicating the reading back to a computer controller through pin connector 52. A surrounding enclosure (not shown) of thermal insulation helps maintain the desired thermal environment, normally in the range of 100° C. A second, similar heater and thermostatic feedback thermocouple 58 is utilized adjacent outlet line 36. A fan 59 enables removal of excess heat.

Tubing enters sampling section 16 from several sample canisters 12 through aperture 28 and is directed to multiposition valve 32 where each tube 42 is connected to respective inlet ports 34. The sample outlet port 62 of the multiposition valve 32 is connected to a sample outlet line 36 as known in the art which extends through a hole in the end cove (on the left hand side as shown in FIGS. 1, 5). The distal end of the sample outlet line 36 (not shown) attaches to a coupling on a cryogenic concentrator.

For ease in moving cart 10 from one location to another, handles 24 are preferably provided on each side end panel 22 (FIGS. 1, 3 and 8). As shown in FIG. 8, each side panel 22 preferably comprises outer skin 22A and inner skin 22B.

Wheels or casters 58, mounted for example on leg pieces 60, are preferably attached to the lower area of the cart 10 (FIGS. 1 and 3). Other means of moving the cart 10 of the invention may be substituted for the wheels 58 if desired, so long as the cart is movable to the site of a GC/MS.

The automatic sample control cart 10 of the invention is preferably used as follows. The cart 10 containing the desired number of canisters 12 which have been purged of contaminant gases and have preferably been evacuated to a negative pressure is taken to a field site. All of the canisters 12 may be used to sample the selected environment, for example, a site suspected of air contamination, as is known in the art. Preferably, one of the canisters 12 is utilized for the purpose of purging, or flushing, lines 42 between samples. Thus, for the embodiment of the cart 10 shown in FIG. 1 having sixteen canister-holding locations, fifteen samples of atmospheric gas may be taken. The sixteenth canister 12 attaches to a sample line which runs to a sixteenth inlet port on the multiposition valve 32 which is used as a blank/purge inlet, and includes a manual flow regulation valve 55 and a shutoff valve 57 in series with the automatic controlled multiposition valve 32. The sixteenth canister 12 is typically filled with scientific grade purified air for cleansing the outlet line 36 between samples.

The process of collecting air samples may be done either by use of the previously generated negative pressure or be means of a filling pump. If a pump is used, the canister 12 may ordinarily be filled up to a pressure of about four atmospheres.

Each of the canisters is connected to an inlet line 42 which is preferably always connected to the multiposition valve 32. The cart 10 is moved adjacent to a cryogenic concentrator which is part of a gas analytic apparatus. The outlet line 36 of the cart is connected at its distal end to an inlet port of the cryogenic concentrator (not shown) and an electrical control and feedback line is connected to pin connector 52 on the cart 10.

An appropriate computer and operative software are actuated to drive the sample processing system. The computer program is capable of directing the multiposition valve 32 in selecting samples from each canister in a desired order. The computer program is also able to control the temperature at the valve 32 and outlet line 36 together with using the feedback thermocouple 56 signal to adjust the power supplied to each heater.

Because the sample canisters ca remain on the cart during the sample analysis process, sample canisters do not get accidentally interchanged. This means that the chain of custody and thus the sample identity, is easily controlled, from sample receiving through canister cleaning without removal of the canisters from the cart.

Specifically included within the scope of the invention herein are carts designed for a different number of canisters than the sixteen canisters shown in the Figures, for example, for four or eight canisters, or more than sixteen canisters. In these cases, it is clear that the amount of space for placement of canisters, and thus the dimensions of the various components of the carts, change in accord with the number of canisters for which the cart is designed. In addition, since the carts of the invention preferably have a number of inlets matching the number of canisters for which the cart is designed a different multiposition valve according to the number of canisters for which the cart is designed is used on the alternate embodiments of the cart of the invention.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An automatic sample control cart, comprising:
   (a) a cart having a base portion with a plurality of wheels adapted to be in contact with a supporting surface and having a sampling section;
   (b) a series of shelf members mounted on said base portion and adapted to support a selected number of sample canisters at particular canister-holding locations;
   (c) an electronically actuated multiposition valve mounted on said cart in said sampling section and operatively connectable to each of said canisters, said valve having one outlet and sufficient inlets so that each canister may be connected to an inlet, wherein gas samples in the canisters may be randomly and selectively accessed using said valve;
   (d) one or more inlet lines mounted on said cart, each of said inlet lines having a proximal end and a distal end, each of said lines being configured to connect to one of said canisters at said proximal end at a canister-holding location and to said valve at said distal end; and
   (e) a heated outlet line connected to said valve and connectable to a cryogenic concentrator, wherein after gas sampling, each of said canisters may be attached to an inlet line and remain on the cart attached to said inlet line during movement to a gas analysis site and for gas analysis, said analysis being performable by selectively accessing each canister so that gas sample from the selected canister is taken via the attached inlet line to said multiposition valve through said outlet line, to a cryogenic concentrator and chemical analyzer.

2. An automatic sample control cart according to claim 1, further comprising a heater for maintaining a temperature of said valve above ambient temperature.

3. An automatic sample control cart according to claim 2, further comprising a heater for maintaining a temperature of said outlet line above ambient temperature.

4. An automatic sample control cart according to claim 3, further comprising a thermocouple adapted to sense the temperature of said valve and said outlet line and to automatically communicate said temperature to a control device.

5. An automatic sample control cart according to claim 1, wherein said valve comprises an electrically controlled multiposition valve.

6. An autosampling device for use in sampling atmospheric gases for the presence of pollutants comprising:
   (a) a movable cart;
   (b) shelf members on said cart having a plurality of canister-holding locations;
   (c) a multiposition valve mounted on said cart and having a plurality of inlet ports and an outlet port;
   (d) a plurality of sample inlet lines mounted on said cart, each of said sample inlet lines being connectable to a canister and extending from a canister-holding location to one of said inlet ports; and
   (e) an outlet sample line extending from the outlet port and being connectable to an inlet of a sample concentrator; wherein said device allows random access to each canister placed on said shelf members and controlled direction of the gases in the canisters to said sample concentrator;
   (f) heating zones operative to maintain a temperature of said valve and said outlet line above ambient temperature, wherein the position of the multiposition valve and the temperatures of the two heated zones may be controlled by a feedback thermocouple adjacent said multiposition valve, wherein after gas sampling, each of said canisters may be attached to an inlet line and remain on the cart attached to said inlet line during movement to a gas analysis site and for gas analysis, said analysis being performable by selectively accessing each canister so that gas sample from the selected canister is taken via the attached inlet line to said multiposition valve through said outlet line, to a cryogenic concentrator and chemical analyzer.

7. An autosampling device for use in sampling atmospheric gases for the presence of pollutants according to claim 6 wherein said plurality comprises sixteen canister-holding locations and there are sixteen sample inlet lines.

8. A method of sampling atmospheric gases for the presence of pollutants and for maintaining sample chain of custody, comprising:
   (a) providing an autosampling device comprising:
      (i) a movable cart;
      (ii) shelf members on said cart having a plurality of canister-holding locations;
      (iii) an electrically actuated multiposition valve mounted on said cart and having a plurality of inlet ports and an outlet port;
      (iv) a plurality of sample lines mounted on said cart, each of said sample lines being connectable to a canister and extending from a canister-holding location to one of said inlet ports;
      (v) an outlet sample line extending from the outlet port and being connectable to an inlet of a sample concentrator; wherein said device allows random access to each canister placed on said shelf members and controlled direction of the gases in the canisters to said sample concentrator;
   (b) collecting air samples in said canisters;
   (c) connecting said canisters to said sample lines;
   (d) connecting said outlet line to a sample concentrator; and
   (e) controlling said multiposition valve to conduct samples from selected canisters sequentially to said outlet line, wherein after gas sampling, each of said canisters may be attached to an inlet line and remain on the cart attached to said inlet line during movement to a gas analysis site and for gas analysis, said analysis being performable by selectively accessing each canister so that gas sample from the selected canister is taken via the attached inlet line to said multiposition valve through said outlet line, to a cryogenic concentrator and chemical analyzer.

* * * * *